US012484863B2

(12) United States Patent
Takahashi et al.

(10) Patent No.: US 12,484,863 B2
(45) Date of Patent: Dec. 2, 2025

(54) X-RAY CT APPARATUS AND CONTROL METHOD OF THE SAME

(71) Applicant: FUJIFILM Healthcare Corporation, Chiba (JP)

(72) Inventors: Isao Takahashi, Kashiwa (JP); Takashi Ishikawa, Kashiwa (JP)

(73) Assignee: FUJIFILM Corporation, Tokyo (JP)

( * ) Notice: Subject to any disclaimer, the term of this patent is extended or adjusted under 35 U.S.C. 154(b) by 189 days.

(21) Appl. No.: 18/481,253

(22) Filed: Oct. 5, 2023

(65) Prior Publication Data

US 2024/0122557 A1 Apr. 18, 2024

(30) Foreign Application Priority Data

Oct. 18, 2022 (JP) ................................ 2022-166568

(51) Int. Cl.
*A61B 6/03* (2006.01)
*A61B 6/40* (2024.01)

(52) U.S. Cl.
CPC ............ *A61B 6/032* (2013.01); *A61B 6/4028* (2013.01)

(58) Field of Classification Search
CPC ..... A61B 6/032; A61B 6/4028; A61B 6/4021; A61B 6/405; A61B 6/44; A61B 6/54
See application file for complete search history.

(56) References Cited

U.S. PATENT DOCUMENTS

2003/0072407 A1* 4/2003 Mihara ................ A61B 6/4028 378/4
2012/0027173 A1* 2/2012 Duerr .................... H01J 35/065 378/62

FOREIGN PATENT DOCUMENTS

JP 2020115975 8/2020

* cited by examiner

*Primary Examiner* — Courtney D Thomas
(74) *Attorney, Agent, or Firm* — JCIPRNET

(57) ABSTRACT

Provided are an X-ray CT apparatus and a control method of the same capable of reducing focal blur even in a case where an X-ray focal spot is moved.
There is provided an X-ray CT apparatus including: an X-ray tube including a cathode that generates an electron beam and an anode that collides with the electron beam to radiate an X-ray; an X-ray detector configured to detect the X-ray; a rotating plate configured to rotate the X-ray tube and the X-ray detector around a subject; and an image processing unit configured to generate a tomographic image of the subject based on projection data acquired by the X-ray detector during rotation of the rotating plate, in which the cathode, which has a plurality of electron sources that are arranged within a plane facing the anode and emit the electron beam, is configured such that a position of an electron source, from which an electron beam is to be emitted, is selectively controlled based on a target position of an X-ray focal spot in the anode.

12 Claims, 8 Drawing Sheets

X-RAY CT APPARATUS AND CONTROL METHOD OF THE SAME

CLAIM OF PRIORITY

The present application claims priority from Japanese Patent Application JP 2022-166568 filed on Oct. 18, 2022, the content of which is hereby incorporated by reference into this application.

BACKGROUND OF THE INVENTION

1. Field of the Invention

The present invention relates to an X-ray computed tomography (CT) apparatus, and more particularly, to control of an X-ray tube.

2. Description of the Related Art

An X-ray CT apparatus generates tomographic images of a subject using projection data that is obtained from multiple directions by rotating an X-ray tube, which irradiates the subject with X-rays, and an X-ray detector, which detects the X-rays transmitted through the subject, around the subject. The generated tomographic image depicts a shape of an organ within the subject and is used for image diagnosis.

The X-ray tube comprises a cathode and an anode, which are held in a vacuum, and causes an electron beam emitted from the cathode to collide with the anode to radiate an X-ray from an X-ray focal spot that is a point of collision of the electron beam. In order to prevent overheating and melting of the anode due to most of the electron beam's energy being converted into heat upon collision with the anode, there are a rotatable anode and an X-ray tube configured to move the X-ray focal spot. In a case where the X-ray focal spot is moved, an apparent size of the X-ray focal spot increases, and this leads to a degradation in the resolution of the tomographic image.

JP2020-115975A discloses an X-ray tube that continuously and periodically moves an X-ray focal spot, in which a movement speed of the X-ray focal spot is determined according to an imaging purpose based on a movement speed at which an anode is not melted and a movement speed at which a predetermined resolution is satisfied.

SUMMARY OF THE INVENTION

However, in JP2020-115975A, a size of the X-ray focal spot varies depending on a position of the X-ray focal spot because a trajectory of electrons emitted from the cathode is changed by an electric field or a magnetic field, and this may result in focal blur. The focal blur causes a degradation in the image quality of the tomographic image.

In that respect, an object of the present invention is to provide an X-ray CT apparatus and a control method of the same capable of reducing focal blur even in a case where an X-ray focal spot is moved.

In order to achieve the above object, according to an aspect of the present invention, there is provided an X-ray CT apparatus comprising: an X-ray tube including a cathode that generates an electron beam and an anode that collides with the electron beam to radiate an X-ray; an X-ray detector configured to detect the X-ray; a rotating plate configured to rotate the X-ray tube and the X-ray detector around a subject; and an image processing unit configured to generate a tomographic image of the subject based on projection data acquired by the X-ray detector during rotation of the rotating plate, in which the cathode, which has a plurality of electron sources that are arranged within a plane facing the anode and emit the electron beam, is configured such that a position of an electron source, from which an electron beam is to be emitted, is selectively controlled based on a target position of an X-ray focal spot in the anode.

Further, according to another aspect of the present invention, there is provided a control method of an X-ray CT apparatus including an X-ray tube including a cathode that generates an electron beam and an anode that collides with the electron beam to radiate an X-ray, an X-ray detector configured to detect the X-ray, a rotating plate configured to rotate the X-ray tube and the X-ray detector around a subject, and an image processing unit configured to generate a tomographic image of the subject based on projection data acquired by the X-ray detector during rotation of the rotating plate, the control method comprising: in the cathode, which has a plurality of electron sources that are arranged within a plane facing the anode and emit the electron beam, selectively controlling a position of an electron source, from which an electron beam is to be emitted, based on a target position of an X-ray focal spot in the anode.

According to the aspects of the present invention, it is possible to provide an X-ray CT apparatus and a control method of the same capable of reducing focal blur even in a case where an X-ray focal spot is moved.

DESCRIPTION OF THE PREFERRED EMBODIMENTS

Figure 1:
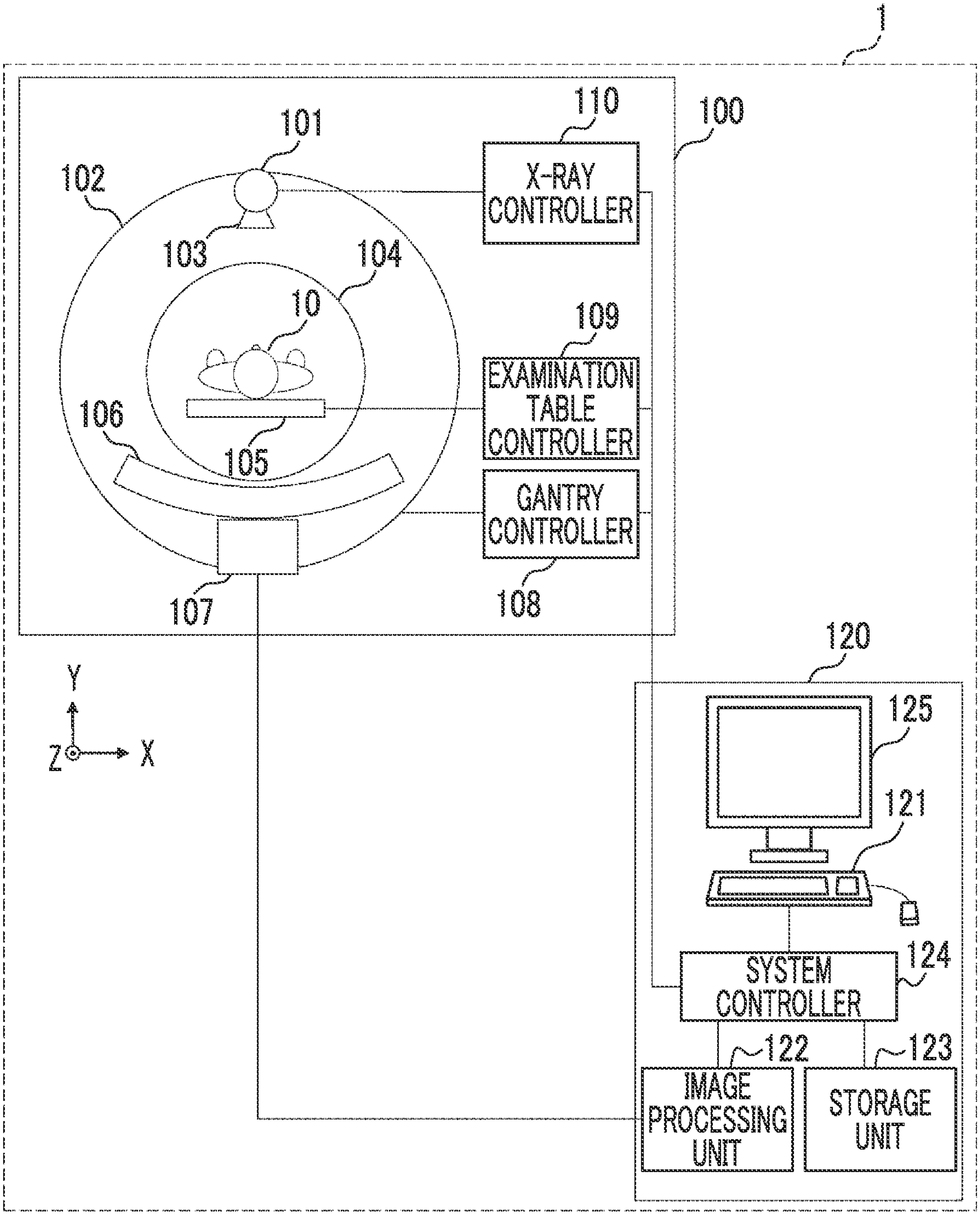
FIG. 1 is a diagram showing an overall configuration of an X-ray CT apparatus.

Hereinafter, preferred embodiments of an X-ray CT apparatus according to the present invention will be described with reference to the accompanying drawings. In the following description and the accompanying drawings, components having the same functional configuration are designated by the same reference numerals, and duplicate description thereof will not be repeated.

An example of an overall configuration of an X-ray CT apparatus 1 will be described with reference to FIG. 1. The X-ray CT apparatus 1 comprises a scan gantry unit 100 and an operation unit 120.

The scan gantry unit 100 comprises an X-ray tube 101, a rotating plate 102, a collimator 103, an X-ray detector 106, a data collection device 107, an examination table device 105, a gantry controller 108, an examination table controller 109, and an X-ray controller 110. The X-ray tube 101 is a device that irradiates a subject 10 mounted on the examination table device 105 with X-rays. The collimator 103 is a device that limits an irradiation range of X-rays. The rotating plate 102 has an opening portion 104 through which the subject 10 mounted on the examination table device 105 enters, and is also equipped with the X-ray tube 101 and the X-ray detector 106 and rotates the X-ray tube 101 and the X-ray detector 106 around the subject 10.

The X-ray detector 106 is a device that is disposed to face the X-ray tube 101 and that measures a spatial distribution of transmitted X-rays by detecting X-rays transmitted through the subject 10. Detection elements of the X-ray detector 106 are arranged two-dimensionally in a rotation direction and a rotation axis direction of the rotating plate 102. The data collection device 107 is a device that collects an X-ray dose detected by the X-ray detector 106 as digital data.

The gantry controller 108 is a device that controls the rotation and the inclination of the rotating plate 102. The examination table controller 109 is a device that controls up, down, front, back, left, and right movements of the examination table device 105. The X-ray controller 110 is a device that controls power to be input to the X-ray tube 101. The gantry controller 108, the examination table controller 109, and the X-ray controller 110 are each, for example, a micro processing unit (MPU).

The operation unit 120 comprises an input unit 121, an image processing unit 122, a display unit 125, a storage unit 123, and a system controller 124. The input unit 121 is a device for inputting the name of the subject 10, examination date and time, imaging conditions, and the like, and specifically, is a keyboard, a pointing device, a touch panel, or the like. The image processing unit 122 is a device that performs computational processing on measurement data sent out from the data collection device 107 to reconstruct a tomographic image or that performs various types of image processing on the tomographic image, and is, for example, a graphics processing unit (GPU) or an MPU. The display unit 125 is a device that displays a tomographic image or the like generated by the image processing unit 122, and specifically, is a liquid crystal display, a touch panel, or the like. The storage unit 123 is a device that stores data collected by the data collection device 107, the tomographic image generated by the image processing unit 122, or the like, and specifically, is a hard disk drive (HDD) or the like. The system controller 124 is a device that controls each unit, and is, for example, a central processing unit (CPU).

By controlling the power to be input to the X-ray tube 101 through the X-ray controller 110 based on the imaging conditions input through the input unit 121, particularly an X-ray tube voltage, an X-ray tube current, and the like, the X-ray tube 101 irradiates the subject 10 with X-rays corresponding to the imaging conditions. The X-ray detector 106 detects the X-rays emitted from the X-ray tube 101 and transmitted through the subject 10 by using the detection elements two-dimensionally arranged, and measures the distribution of the transmitted X-rays. The rotating plate 102 is controlled by the gantry controller 108 and rotates based on imaging conditions input through the input unit 121, particularly the rotation speed and the like. The examination table device 105 is controlled by the examination table controller 109 and operates based on imaging conditions input through the input unit 121, particularly a spiral pitch and the like.

By repeating X-ray irradiation from the X-ray tube 101 and X-ray measurement by the X-ray detector 106 together with the rotation of the rotating plate 102, projection data from multiple directions is acquired, and the acquired projection data is transmitted to the image processing unit 122. The image processing unit 122 reconstructs the tomographic image by performing back-projection processing on the transmitted projection data from multiple directions. The reconstructed tomographic image is displayed on the display unit 125.

Figure 2:
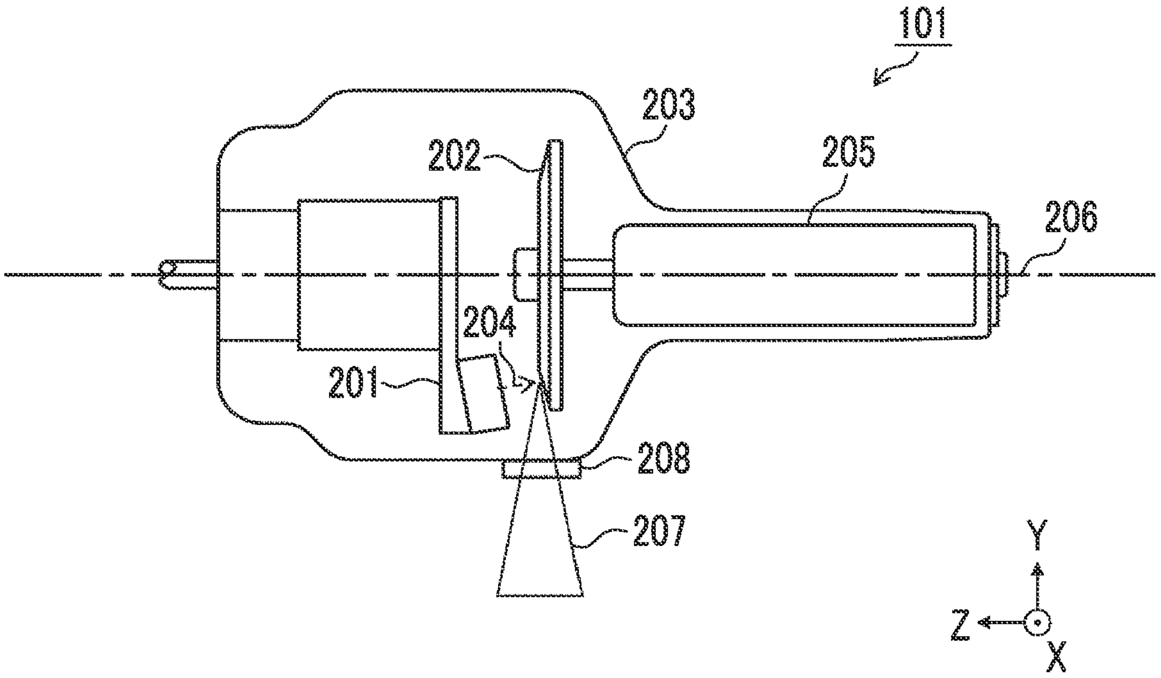
FIG. 2 is a diagram showing an example of an overall configuration of an X-ray tube.

An example of an overall configuration of the X-ray tube 101 will be described with reference to FIG. 2. The X-ray tube 101 has a cathode 201, an anode 202, an outer enclosure 203, and a radiation window 208. The cathode 201 generates an electron beam 204 and comprises, for example, a cold cathode that performs field emission of electrons through field concentration. A detailed configuration of the cathode 201 will be described below with reference to FIG. 3.

The anode 202 is an electrode to which a positive potential is applied relative to the cathode 201, and has, for example, a disc shape and comprises a target and an anode substrate. The target is made of a material having a high melting point and a large atomic number, such as tungsten. The electron beam 204 from the cathode 201 collides with the target, whereby the X-ray is radiated from an X-ray focal spot which is a point of collision of the electron beam 204. The anode substrate is made of a material having a high thermal conductivity, such as copper, and holds the target. The target and the anode substrate have the same potential.

In order to prevent overheating and melting of the anode 202 due to most of the electron beam 204's energy being converted into heat upon collision with the anode 202, the anode 202 may be rotatable. For example, the anode 202 is rotatably supported by a rotation support portion 205 and rotates about a rotation axis 206. That is, by rotating the anode 202, the X-ray focal spot, which is the point of collision of the electron beam 204, always moves, so that a temperature of the X-ray focal spot can be kept lower than the melting point of the target, and the overheating and melting of the anode 202 can be prevented.

The outer enclosure 203 holds the cathode 201 and the anode 202 in a vacuum atmosphere in order to electrically insulate the cathode 201 and the anode 202 from each other. The radiation window 208 is provided on the outer enclosure 203 in order to irradiate the subject 10 with an X-ray 207, which is a part of X-rays emitted from the X-ray focal spot, and is made of, for example, a material having a small atomic number, such as beryllium.

A configuration example of the cathode 201 will be described with reference to FIG. 3. The cathode 201 has a plurality of electron sources 211 and gate electrodes 212. The electron sources 211 are each formed by sharpening metals, such as nickel or molybdenum, or a carbon nanotube (CNT) such that field emission of electrons is performed through field concentration, and are arranged within a plane facing the anode 202.

The gate electrode 212 is disposed near the sharp tip of the electron source 211 and is connected to a gate power supply 213 via a switch 214. In a case where the switch 214 is turned on, a voltage is applied to the gate electrode 212 from the gate power supply 213, an electric field is concentrated on the electron source 211 located near the gate electrode 212 to which the voltage is applied, and field emission of electrons is performed from the electron source 211 on which the electric field is concentrated, whereby the electron beam 204 is generated. That is, the position of the electron source 211 from which the electron beam 204 is to be emitted can be selectively controlled through the on-off control of a plurality of the switches 214. The on-off control of the switch 214 is performed by the X-ray controller 110 or the system controller 124.

Figure 3:
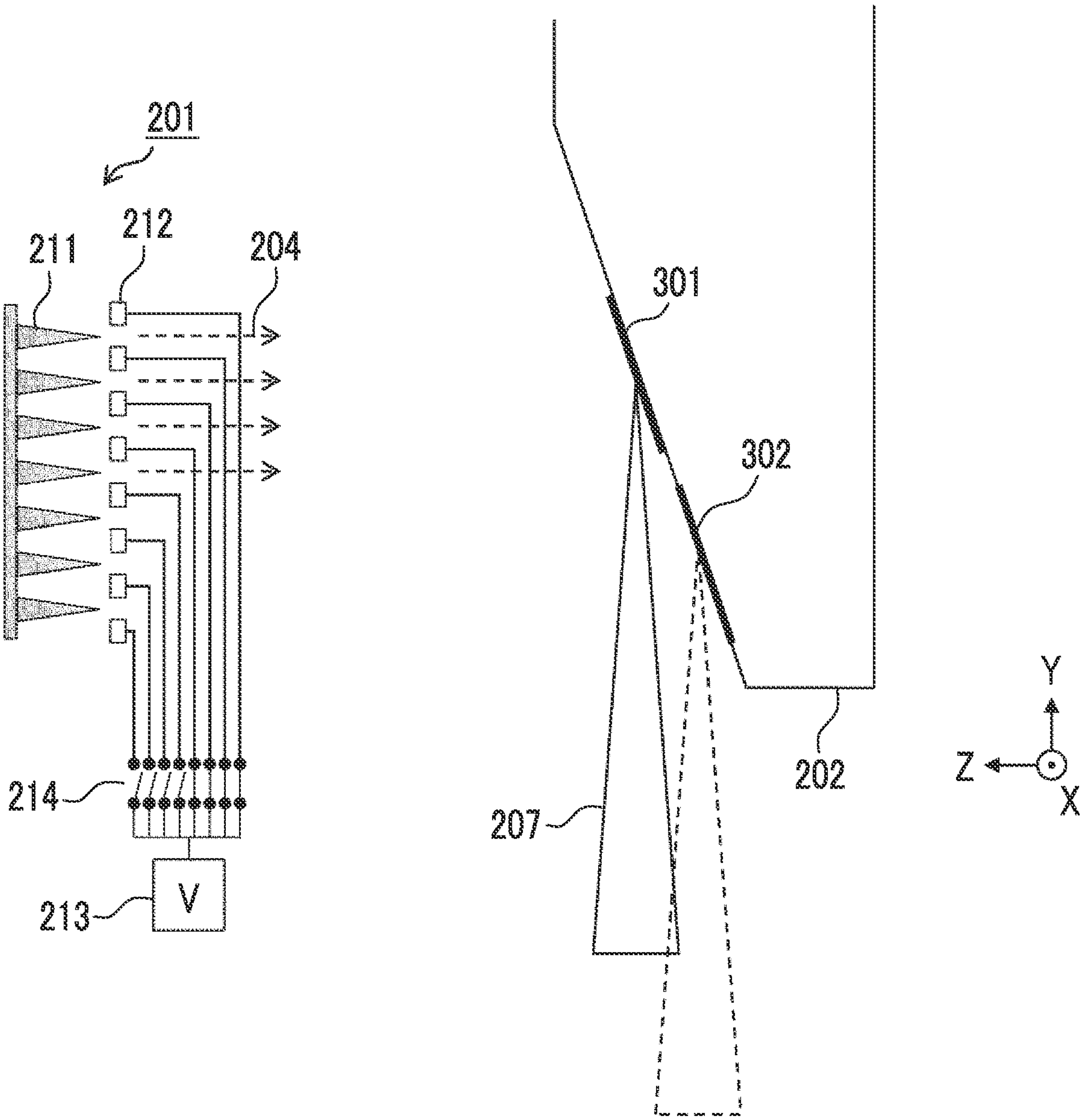
FIG. 3 is a diagram showing a configuration example of a cathode.

FIG. 3 shows an example of the electron beam 204 emitted from four upper electron sources 211 selected from among seven electron sources 211. The electron beam 204 emitted from the four upper electron sources 211 collides with a first focal spot 301 on the anode 202 to generate the X-ray 207. In a case where the switches 214 are switched and the electron beam 204 is emitted from four lower electron sources 211, the X-ray 207 is generated from a second focal spot 302. That is, by selectively controlling the position of the electron source 211 from which the electron beam 204 is to be emitted, the X-ray focal spot can be moved without bending the trajectory of the electron beam 204. In addition, since the X-ray focal spot is moved without bending the trajectory of the electron beam 204, the size of the X-ray focal spot after the movement is the same as the size before the movement, and focal blur can be prevented.

An example of a flow of processing executed in Example 1 will be described step by step with reference to FIG. 4.

S401

The system controller 124 receives an imaging instruction input by a user via the input unit 121. The user inputs the imaging conditions to the input unit 121 together with the imaging instruction.

S402

The system controller 124 acquires the target position of the X-ray focal spot included in the imaging condition input in S401. For example, the target position of the X-ray focal spot set in accordance with the projection angle of the X-ray is acquired.

S403

The system controller 124 or the X-ray controller 110 selectively controls the position of the electron source 211 from which the electron beam 204 is to be emitted, based on the target position of the X-ray focal spot acquired in S402.

Figure 5:
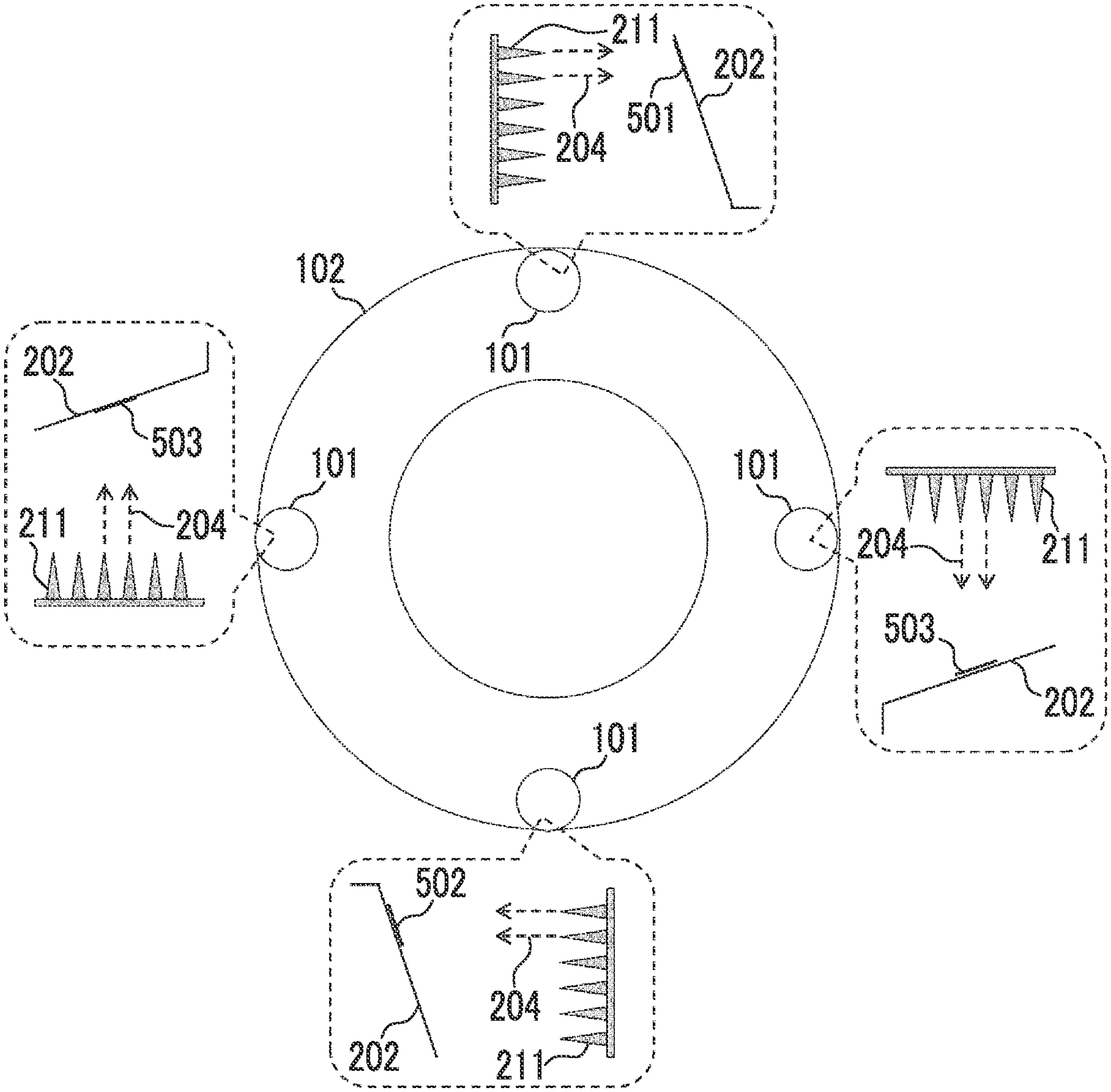
FIG. 5 is a diagram illustrating selective control of an electron beam emission position with respect to a projection angle.

The selective control of an electron beam emission position with respect to the projection angle will be described with reference to FIG. 5. In a case where the target position of the X-ray focal spot is set in accordance with the projection angle of the X-ray, the system controller 124 or the X-ray controller 110 controls the switch 214 such that the electron beam 204 is emitted from the electron source 211 corresponding to each target position. For example, in a case where a first target position 501 is set for the X-ray tube 101 located at the 0 o'clock position, the switch 214 is controlled such that the electron beam 204 is emitted from the electron source 211 that emits the electron beam 204 which reaches the first target position 501. Further, in a case where a second target position 502 is set for the X-ray tube 101 located at the 6 o'clock position, the electron beam 204 is emitted from the electron source 211 corresponding to the second target position 502. Further, in a case where a third target position 503 between the first target position 501 and the second target position 502 is set for the X-ray tube 101 located at the 3 o'clock position and the 9 o'clock position, the electron beam 204 is emitted from the electron source 211 corresponding to the third target position 503. The electron beam 204 is emitted toward the target position set for each projection angle, whereby the subject 10 is irradiated with the X-ray from each target position.

Figure 4:
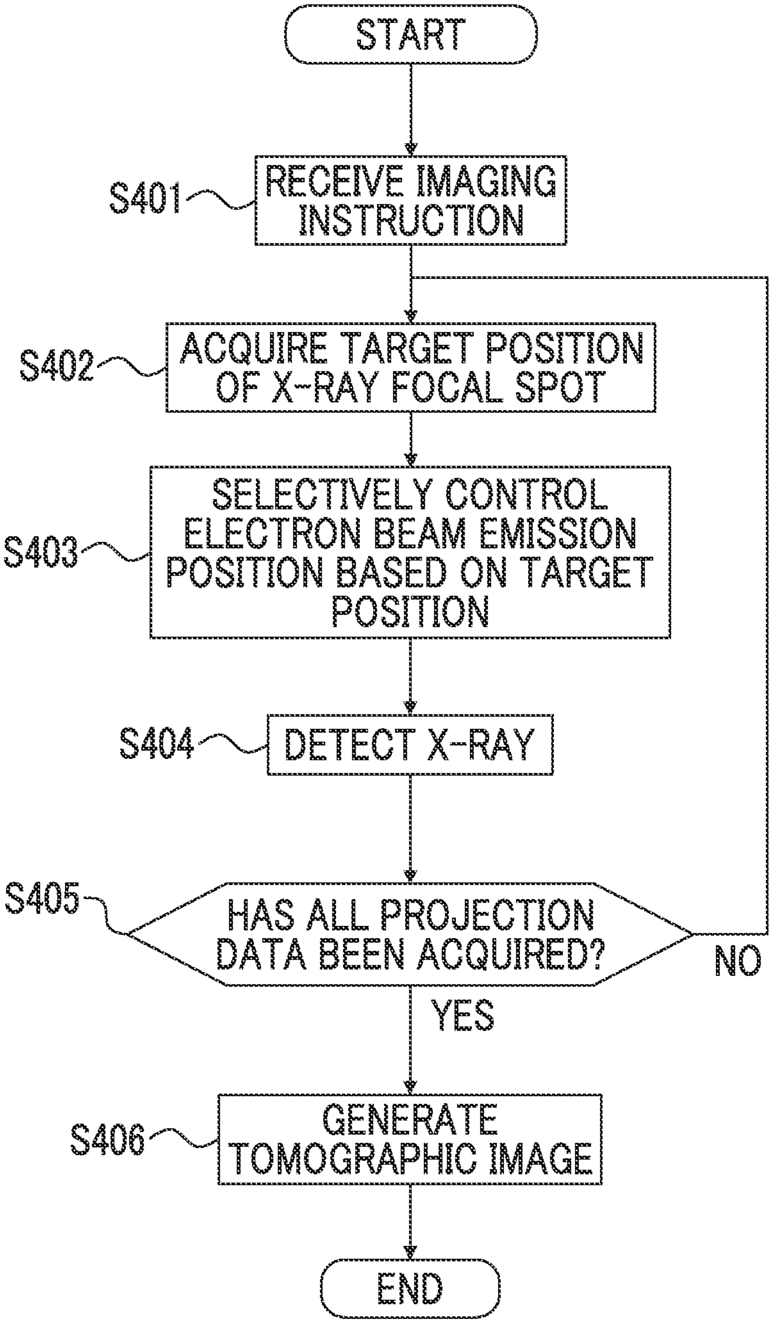
FIG. 4 is a diagram showing an example of a flow of processing of Example 1.

Return to the description of FIG. 4.

S404

The X-ray detector 106 detects the X-ray emitted in S403. The detected data is transmitted to the image processing unit 122 as the projection data. The position of the collimator 103 or the X-ray tube 101 may be controlled in conjunction with the movement of the X-ray focal spot.

Figure 6:
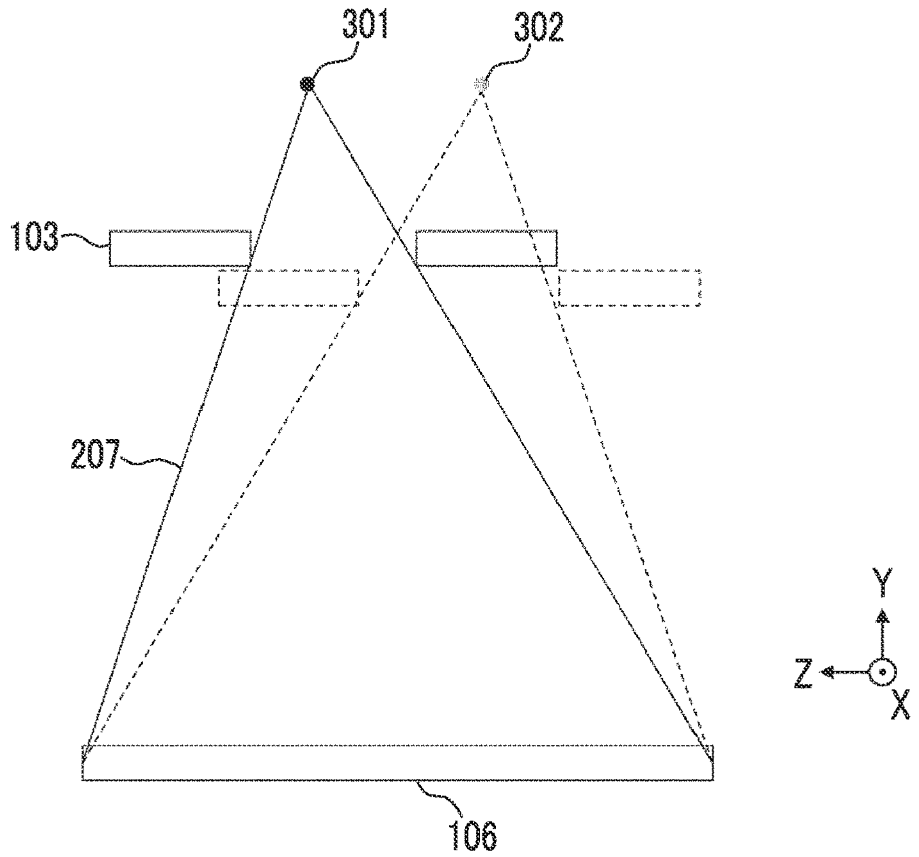
FIG. 6 is a diagram illustrating position control of a collimator with respect to a position of an X-ray focal spot.

The position control of the collimator 103 with respect to the position of the X-ray focal spot will be described with reference to FIG. 6. The system controller 124 controls a position of the collimator 103 in synchronization with the movement of the X-ray focal spot to make the irradiation region of the X-ray 207 always correspond to the X-ray detector 106. In FIG. 6, the collimator 103 that limits the irradiation region of the X-ray 207 emitted from the first focal spot 301 is shown by a solid line, and the collimator 103 that limits the irradiation region of the X-ray 207 from the second focal spot 302 is shown by a dotted line. By making the irradiation region of the X-ray 207 always correspond to the X-ray detector 106, it is possible to reduce unnecessary exposure to the subject 10 without the need to expand the irradiation region.

Figure 7:
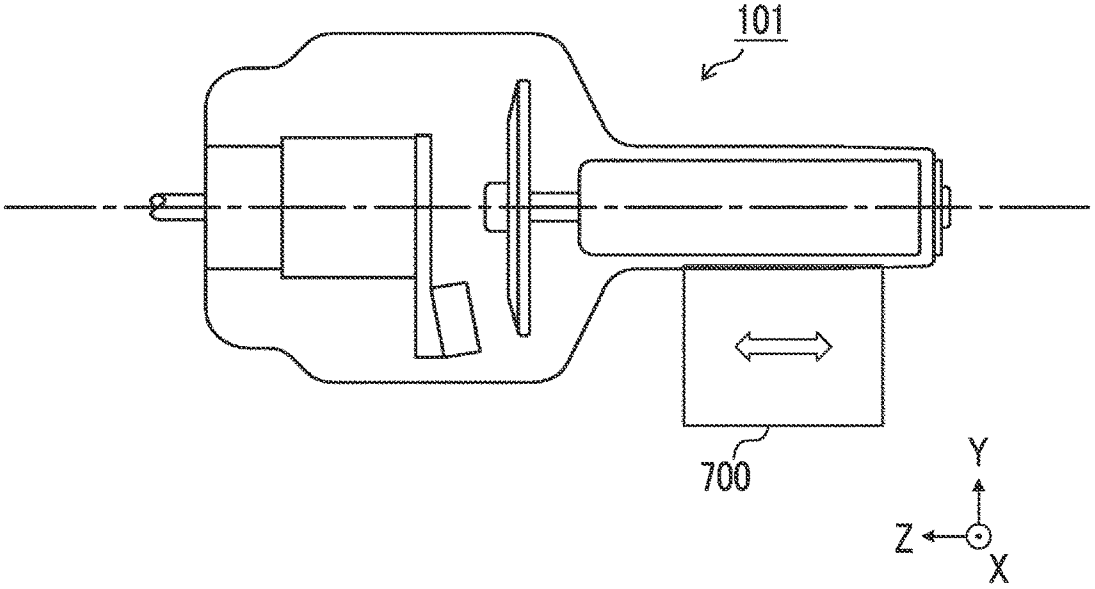
FIG. 7 is a diagram illustrating position control of the X-ray tube with respect to the position of the X-ray focal spot.

The position control of the X-ray tube 101 with respect to the position of the X-ray focal spot will be described with reference to FIG. 7. The X-ray tube 101 is provided with an X-ray tube movement unit 700 that moves the position of the X-ray tube 101 in a Z direction. The system controller 124 controls the X-ray tube movement unit 700 in synchronization with the movement of the X-ray focal spot to keep a constant position of the X-ray focal spot visible from the X-ray detector 106. By keeping the constant position of the X-ray focal spot visible from the X-ray detector 106, it is possible to facilitate processing of generating the tomographic image even in a case where the X-ray focal spot is moved.

Return to the description of FIG. 4.

S405

The system controller 124 determines whether or not all the projection data has been acquired. In a case where all the projection data has been acquired, the process proceeds to S406; otherwise, the process returns to S402.

S406

The image processing unit 122 generates the tomographic image using the projection data acquired in S404. The tomographic image may be generated in response to the movement of the X-ray focal spot. The generated tomographic image is displayed on the display unit 125 or stored in the storage unit 123.

According to the flow of the processing described with reference to FIG. 4, for example, a constant size of the X-ray focal spot is kept before and after the movement of the X-ray focal spot even in a case where the X-ray focal spot is moved in accordance with the projection angle of the X-ray, and the focal blur is suppressed, so that the image quality of the tomographic image can be maintained. It should be noted that the selective control of the emission position of the electron beam 204 is not limited to making the X-ray focal spot correspond to the projection angle of the X-ray.

Figure 8:
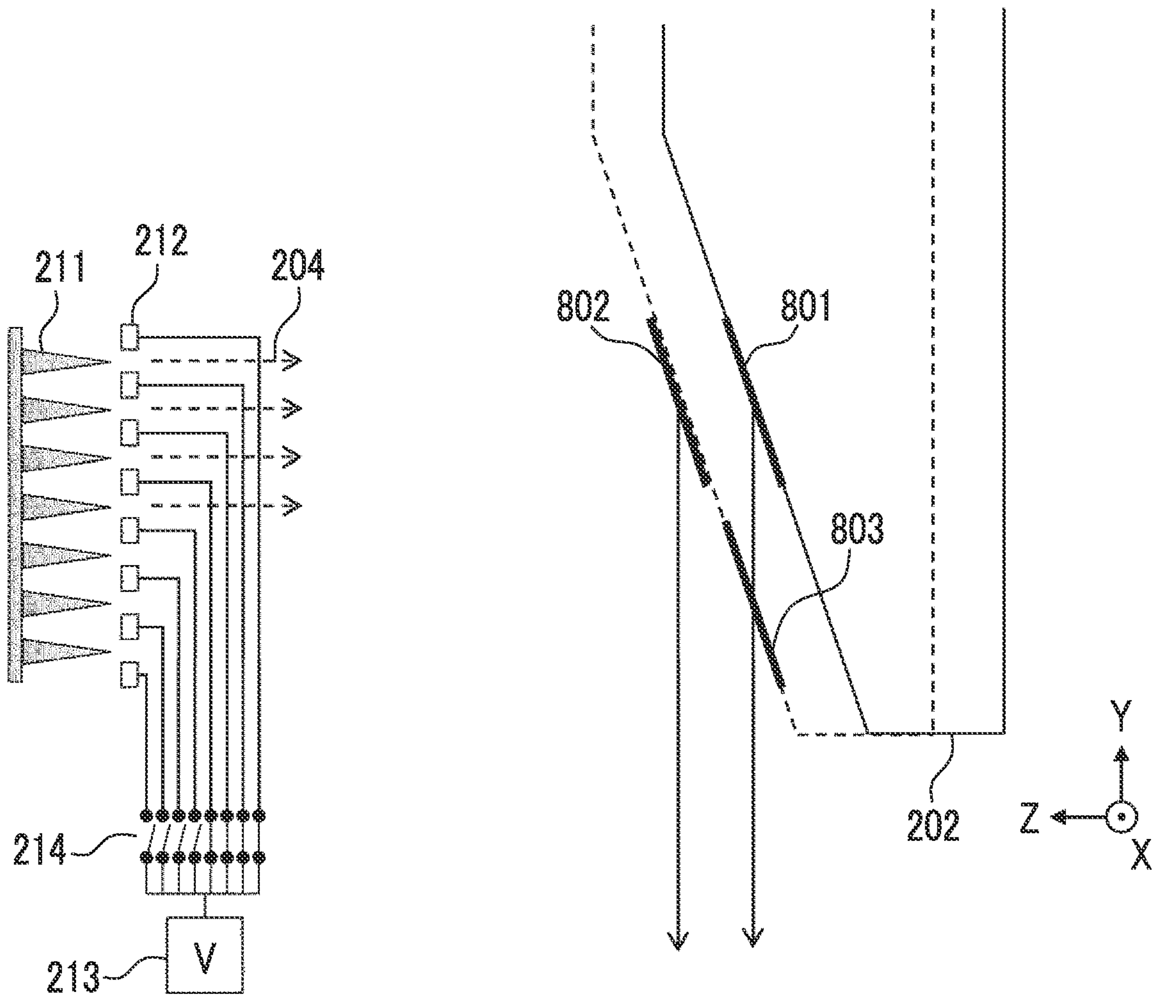
FIG. 8 is a diagram illustrating selective control of the electron beam emission position with respect to focal spot movement due to thermal expansion of an anode.

The selective control of the emission position of the electron beam 204 with respect to the focal spot movement due to the thermal expansion of the anode 202 will be described with reference to FIG. 8. In a case where the anode 202 heated by the collision of the electron beam 204 thermally expands, the position of the X-ray focal spot may move. FIG. 8 shows an example of a thermal expansion-induced focal spot 802, which is moved from a position of an initial focal spot 801 by the thermal expansion of the anode 202. Since the movement of the focal spot degrades the image quality of the tomographic image, it is desirable for the position of the thermal expansion-induced focal spot 802 to be corrected.

Therefore, the position of the focal spot is corrected by measuring a movement amount of the focal spot due to the thermal expansion of the anode 202 and selectively controlling the emission position of the electron beam 204 based on the measured movement amount. For example, the position of the thermal expansion-induced focal spot 802 in a case where the electron beam 204 is emitted from the four upper electron sources 211 of the seven electron sources 211 is corrected to a position of a corrected focal spot 803 by switching the switches 214 and emitting the electron beam 204 from the four lower electron sources 211. In this case, the position of the corrected focal spot 803 is set as the target position. Since the correction of the position from the thermal expansion-induced focal spot 802 to the corrected focal spot 803 is performed by the selective control of the emission position of the electron beam 204, which does not require the bending of the trajectory of the electron beam 204, a constant size of the X-ray focal spot is kept, and the focal blur is suppressed.

The selective control of the emission position of the electron beam 204 may be performed based on the movement amount of the focal spot measured in a short time or on the movement amount of the focal spot measured during half or full rotation of the rotating plate 102. In addition, in a case where the measured movement amount is minimal and is equal to or less than a predetermined threshold value, there is no need to perform the selective control of the emission position of the electron beam 204. Further, an initial value of the emission position of the electron beam 204 may be set in advance based on the position of the focal spot predicted from the history of X-ray irradiation.

Figure 9:
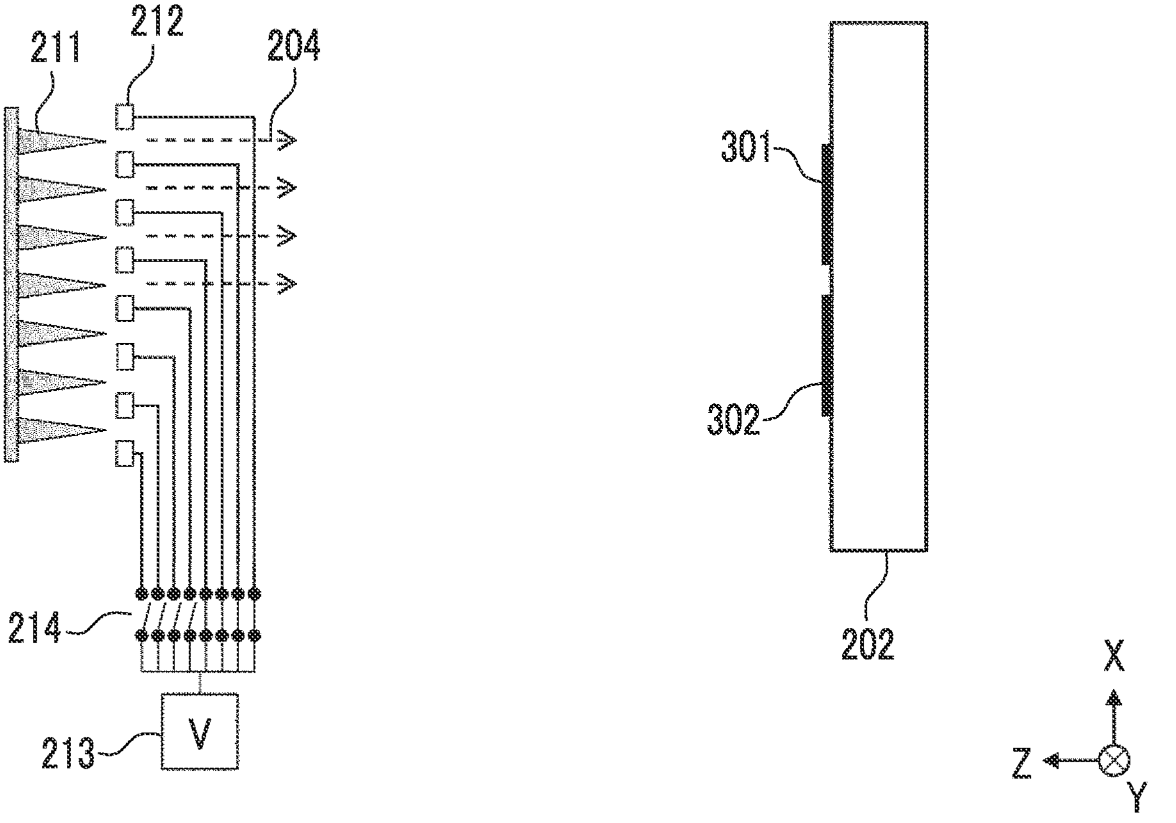
FIG. 9 is a diagram illustrating selective control of the electron beam emission position in a flying focal spot.

Selectively controlling the emission position of the electron beam 204 in a flying focal spot (FFS) will be described with reference to FIG. 9. In the FFS, in order to improve the resolution of the tomographic image, the X-ray focal spot is periodically moved in the rotation direction of the rotating plate 102 during scanning. That is, the positions of the first focal spot 301 and of the second focal spot 302 shown in FIG. 9 are alternately switched as the target positions. The X-ray is emitted in a direction orthogonal to a paper surface of FIG. 9, and the plurality of electron sources 211 are arranged in the rotation direction of the rotating plate 102.

In the FFS, since the position of the X-ray focal spot is also moved by emitting the electron beam 204 from the electron source 211 corresponding to the target position, a constant size of the X-ray focal spot is kept before and after the movement, and the focal blur is suppressed.

The embodiments of the present invention have been described above. It should be noted that the present invention is not limited to the above-described embodiments, and the components can be modified and embodied without departing from the gist of the invention. In addition, a plurality of components disclosed in the above-described embodiments may be combined as appropriate. Further, some components may be deleted from all the components described in the above-described embodiments.

Explanation of References

1: X-ray CT apparatus
10: subject
100: scan gantry unit
101: X-ray tube
102: rotating plate
103: collimator
104: opening portion
105: examination table device
106: X-ray detector
107: data collection device
108: gantry controller
109: examination table controller
110: X-ray controller
120: operation unit
121: input unit
122: image processing unit
123: storage unit
124: system controller
125: display unit
201: cathode
202: anode
203: outer enclosure
204: electron beam
205: rotation support portion
206: rotation axis
207: X-ray
208: radiation window
211: electron source
212: gate electrode
213: gate power supply
214: switch
301: first focal spot
302: second focal spot
501: first target position
502: second target position
503: third target position
700: X-ray tube movement unit
801: initial focal spot
802: thermal expansion-induced focal spot
803: corrected focal spot

What is claimed is:

1. An X-ray CT apparatus comprising:

an X-ray tube including a cathode that generates an electron beam and an anode that collides with the electron beam to radiate an X-ray;

an X-ray detector configured to detect the X-ray;

a rotating plate configured to rotate the X-ray tube and the X-ray detector around a subject; and an image processing unit configured to generate a tomographic image of the subject based on projection data acquired by the X-ray detector during rotation of the rotating plate, wherein the cathode, which has a plurality of electron sources that are arranged within a plane facing the anode and emit the electron beam, is configured such that a position of an electron source, from which an electron beam is to be emitted, is selectively controlled based on a target position of an X-ray focal spot in the anode.

2. The X-ray CT apparatus according to claim 1, wherein the cathode is configured such that the position of the electron source, from which the electron beam is to be emitted, is selectively controlled based on a target position set in accordance with a projection angle of the X-ray.

3. The X-ray CT apparatus according to claim 2, further comprising:

a collimator configured to be moved in conjunction with movement of the X-ray focal spot.

4. The X-ray CT apparatus according to claim 2, further comprising:

an X-ray tube movement unit configured to move the X-ray tube in conjunction with movement of the X-ray focal spot.

5. The X-ray CT apparatus according to claim 1, wherein the cathode is configured such that the position of the electron source, from which the electron beam is to be emitted, is selectively controlled based on a target position set in accordance with thermal expansion of the anode.

6. The X-ray CT apparatus according to claim 1, wherein the cathode is configured such that the position of the electron source, from which the electron beam is to be emitted, is selectively controlled based on target positions alternately set in a rotation direction of the rotating plate.

7. The X-ray CT apparatus according to claim 1, wherein the cathode includes a cold cathode that performs field emission of electrons through field concentration.

8. The X-ray CT apparatus according to claim 1, further comprising:

a controller configured to selectively control the position of the electron source, from which the electron beam is to be emitted.

9. The X-ray CT apparatus according to claim 1, wherein the plurality of electron sources are arranged in a radial direction of the rotating plate.

10. The X-ray CT apparatus according to claim 1, wherein the plurality of electron sources are arranged in a rotation direction of the rotating plate.

11. The X-ray CT apparatus according to claim 1, wherein the X-ray tube includes only one X-ray tube.

12. A control method of an X-ray CT apparatus including an X-ray tube including a cathode that generates an electron beam and an anode that collides with the electron beam to radiate an X-ray, an X-ray detector configured to detect the X-ray, a rotating plate configured to rotate the X-ray tube and the X-ray detector around a subject, and an image processing unit configured to generate a tomographic image of the subject based on projection data acquired by the X-ray detector during rotation of the rotating plate, the control method comprising:

in the cathode, which has a plurality of electron sources that are arranged within a plane facing the anode and emit the electron beam, selectively controlling a position of an electron source, from which an electron beam is to be emitted, based on a target position of an X-ray focal spot in the anode.

* * * * *